| United States Patent [19] | [11] | 4,432,974 |
|---|---|---|
| Haber | [45] | Feb. 21, 1984 |

[54] ANTIINFLAMMATORY AND/OR ANALGESIC 2,3-DIARYL-5-SILYL THIOPHENES

[75] Inventor: Stephen B. Haber, Wilmington, Del.

[73] Assignee: E. I. Du Pont de Nemours and Company, Wilmington, Del.

[21] Appl. No.: 354,643

[22] Filed: Mar. 4, 1982

[51] Int. Cl.³ .................. A61K 31/38; A61K 31/44; C07F 7/08; C07F 7/18

[52] U.S. Cl. .................................. 424/184; 546/14; 549/4

[58] Field of Search .............. 549/4; 546/14; 424/184

[56] References Cited

U.S. PATENT DOCUMENTS 2,640,833   6/1953   DiGiorgio ............................. 549/4
2,645,644   7/1953   DiGiorgio ............................. 549/4

OTHER PUBLICATIONS

Eaborn et al., J. Chem. Soc., (1961) pp. 4921–4927.
S. Hauptmann et al., J. Prakt. Chem. 314, 499–506 (1972).
J. L. Melles et al., Rec. Trav. Chim., 72, 314–328 (1953).
D. Habich et al., Synthesis, 841–876 (1979).
T. Kauffmann et al., Tet. Lett., 4039–4042 (1973).
F. H. Pinkerton et al., J. Het. Chem., 9, 725–728 (1972).
Slocum et al., J. Org. Chem., 41, 3668 (1976).
Knight et al., Tet. Lett., 21, 5051 (1980).

*Primary Examiner*—Richard Raymond

[57] ABSTRACT

2,3-Diaryl-5-silyl thiophenes, such as 2,3-bis(4-methoxyphenyl)-5-(trimethylsilyl)thiophene; 2,3-bis(4-methoxyphenyl)-5-(ethenyldimethylsilyl)thiophene; and 2,3-bis(4-methoxyphenyl)-5-[(2-propenyl)dimethylsilyl]-thiophene, are useful in the treatment of inflammation and/or pain.

12 Claims, No Drawings

ANTIINFLAMMATORY AND/OR ANALGESIC 2,3-DIARYL-5-SILYL THIOPHENES

BACKGROUND OF THE INVENTION

1. Field of Invention

This invention relates to diaryl thiophenes, their preparation, pharmaceutical compositions containing them and methods of using them to treat inflammation and/or pain in mammals. More particularly, this invention relates to antiinflammatory and/or analgesic 2,3-diaryl-5-silyl thiophenes.

2. Prior Art

There is a continuing need for safe and effective antiinflammatory agents. Inflammation is a disease process characterized by redness, fever, swelling, and pain. Arthritis, in its various forms, is the most prevalent, chronic, and severe of the inflammatory diseases. Traumatic injury and infection also involve inflammation, and antiinflammatory drugs are often used in their treatment. The usefulness of most commercial antiinflammatories is limited because of toxicity and adverse side-effects. Many produce gastric irritation and other effects, such as changes in blood cells and central nervous system. Adreno-cortical steroids produce gastric irritation and suppression of normal adrenal function.

The present invention results from efforts to develop new antiarthritic compounds with good antiinflammatory activity and minimal side effects that could be more effective in treating arthritis than presently available drugs.

In addition to antiinflammatory properties, some compounds of this invention have analgesic activity. This additional property is desirable in treatment of arthritis or related diseases; however, such compounds can be employed solely to alleviate pain.

A number of references including J. L. Melles and H. J. Becker, *Rec. Trav. Chim.*, 72, 314 (1953) and S. Hauptmann and E. M. Werner, *J. Prakt. Chem.*, 314, 499 (1972) describe the preparation of 2,3-diaryl thiophenes.

The use of the trialkylsilyl group to trap reactive carbanions and hence its introduction onto aromatic nuclei is well known in the chemical literature. Examples may be found in D. Häbich and F. Effenberger, *Synthesis*, 841 (1979) and T. Kauffmann and A. Mitschker, *Tet. Lett.*, 4039 (1973). The preparation of a 2-trimethylsilyl-5-aryl thiophene by the reaction of 5-lithio-2-trimethylsilyl thiophene with 1,3-dicyanotetrachlorobenzene is described in F. H. Pinkerton and S. F. Thames, *J. Het. Chem.*, 9, 725 (1972).

SUMMARY OF THE INVENTION

According to the present invention there is provided a compound having the formula:

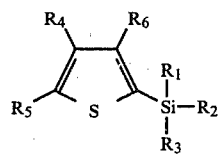
(I)

wherein $R_1$, $R_2$ and $R_3$ are independently H, alkoxy of 1-2 carbon atoms, alkyl of 1-7 carbon atoms optionally substituted with halogen, preferably fluorine, alkenyl of 2-7 carbon atoms, phenyl or benzyl, with the proviso that the sum of the number of carbon atoms in $R_1$, $R_2$ and $R_3$ must be at least 1 and not greater than 9 with the additional proviso that no more than 2 or $R_1$, $R_2$ and $R_3$ are alkoxy;

$R_4$ and $R_5$ are independently pyridyl or

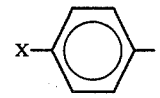

where X is H, F, Cl, $R_7$, $OR_7$, $S(O)_nR_7$ or

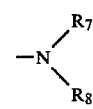

where $n=0$, 1 or 2; $R_7$=alkyl of 1-2 carbon atoms and $R_8$=alkyl of 1-2 carbon atoms;

with the proviso that $R_4$ and $R_5$ cannot both be

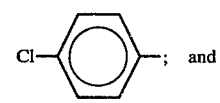; and $R_6$ is H, or alkyl of 1-2 carbon atoms; or a pharmaceutically suitable salt thereof.

Also provided are pharmaceutical compositions containing at least one of the aforesaid compounds and methods of using them to treat inflammation and/or alleviate pain in mammals.

There is also provided a process for preparing the aforesaid compounds which comprises:

reacting a compound of the formula:

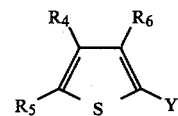

wherein $R_4$, $R_5$ and $R_6$ are as defined above; and

Y is H or Br, with a suitable strong base or other metallating agent and then reacting the resultant intermediates with $R_1R_2R_3$ silyl halide where $R_1$, $R_2$ and $R_3$ are as defined above.

Preferred Scope

Compounds of preferred scope are those of the formula:

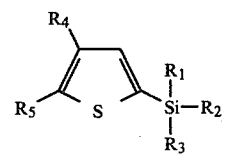
(Ia)

where $R_4$ and $R_5$ are independently

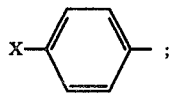

where
X is H, $OR_7$ or $(CH_3)_2N-$ where $R_7$ is alkyl of 1–2 carbon atoms; and/or $R_1$, $R_2$ and $R_3$ are independently H, alkyl of 1–3 carbon atoms, or alkenyl of 2–3 carbon atoms, with the proviso that the sum of the number of carbon atoms in $R_1$, $R_2$ and $R_3$ must be at least 2 and not greater than 5.

More preferred compounds are compounds of Formula Ia where:

$R_4$ and $R_5$ are independently

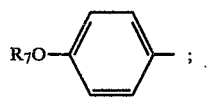

where
$R_7$ is alkyl of 1–2 carbon atoms; and
$R_1$, $R_2$ and $R_3$ are independently H, alkyl of 1–3 carbon atoms, or alkenyl of 2–3 carbon atoms, with the proviso that the sum of the number of carbon atoms in $R_1$, $R_2$ and $R_3$ must be at least 2 and not greater than 5.

Most preferred compounds are compounds of Formula Ia where:

$R_4$ and $R_5$ are both

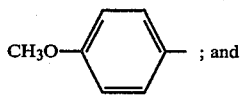

; and $R_1$, $R_2$ and $R_3$ are independently alkyl of 1–2 carbon atoms or alkenyl of 2–3 carbon atoms, with the proviso that the sum of carbon atoms in $R_1$, $R_2$ and $R_3$ is no greater than 5.

Specifically preferred compounds are:
(1) 2,3-bis(4-methoxyphenyl)-5-(trimethylsilyl)thiophene;
(2) 2,3-bis(4-methoxyphenyl)-5-(ethenyldimethylsilyl)thiophene; and
(3) 2,3-bis(4-methoxyphenyl)-5-[(2-propenyl)dimethylsilyl]thiophene.

Pharmaceutical Salts

Pharmaceutically suitable salts and their preparation are well known to those skilled in pharmaceuticals and any can be used in the present invention. Suitable salts of compounds where $R_4$ or $R_5$ is pyridyl or

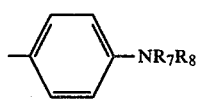

include pharmaceutically suitable acid addition salts, preferably formed from mineral acid and include hydrochloride, nitrate and sulfate. The acid used preferably has a pKa of not greater than 2.5.

Synthesis

The compounds of the invention may be prepared by the following reactions:

Method A

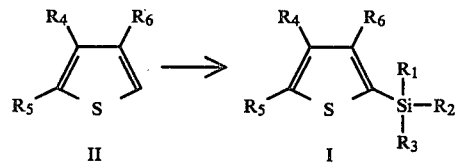

A 2,3-diarylthiophene II is reacted with a strong base such a n-butyl lithium or t-butyl lithium in a solvent such as tetrahydrofuran, toluene or diethyl ether, optionally in the presence of a complexing agent such as tetramethylethylenediamine and then treated with a $R_1R_2R_3$ silyl halide such as trimethyl silyl chloride to give a compound of Formula I. The reaction can be carried out at a temperature from $-78°$ to $110°$ C.

Method B

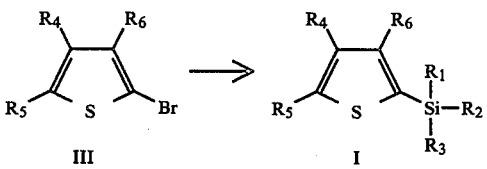

A 2-bromo-4,5-diarylthiophene III is treated with magnesium or a strong base such as n-butyl lithium or t-butyl lithium in a solvent such as tetrahydrofuran, diethyl ether or toluene, optionally in the presence of a complexing agent such as tetramethylethylenediamine at a temperature from $-78°$ to $65°$ C. and is then treated with a $R_1R_2R_3$ silyl halide such as trimethyl silyl chloride to give a compound of Formula I.

Method C

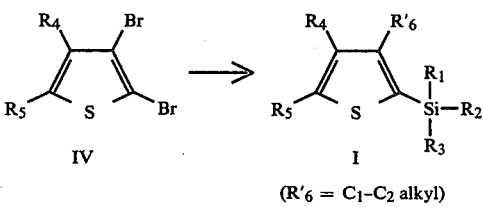

($R'_6 = C_1-C_2$ alkyl)

A dibromothiophene IV in a solvent such as diethyl ether or tetrahydrofuran at a temperature from $-78°$ to $35°$ C. is metallated with a reagent such as n-butyl lithium or magnesium and then treated with a $R_1R_2R_3$ silyl halide such as trimethyl silyl chloride. The resultant intermediate is further treated with a reagent such as n-butyl lithium or magnesium and then with an alkylating agent to give a compound of Formula I where $R_6'$ is alkyl of 1–2 carbon atoms.

Method D

A 2,3-diarylthiophene II is reacted with a strong base such as n-butyl lithium or t-butyl lithium in a solvent such as tetrahydrofuran, diethyl ether or toluene, optionally in the presence of a complexing agent such as tetramethylethylenediamine, and then treated with $R_1R_2$ silyl dichloride. The resultant intermediate is then treated with a reducing agent such as lithium aluminum hydride or di-isobutylaluminum hydride to give a compound of Formula I.

Method E

A 2-bromo-4,5-diarylthiophene III is treated with magnesium or a strong base such as n-butyl lithium or t-butyl lithium in a solvent such as tetrahydrofuran, diethyl ether or toluene, optionally in the presence of a complexing agent such as tetramethylethylenediamine, and then reacted with $R_1R_2$ silyl dichloride. The resultant intermediate is then treated with a reducing agent such as lithium aluminum hydride or di-isobutylaluminum hydride to give a compound of Formula I.

The compounds of the invention and their synthesis are further illustrated by the following examples. All temperatures are in degrees Centigrade.

EXAMPLE 1

2,3-Bis(4-methoxyphenyl)-5-(trimethylsilyl)thiophene 2,3-Bis(4-methoxyphenyl)thiophene (5.92 g, 20 mmole) was dissolved in 100 ml toluene and the volume reduced by approximately ¾ by distillation. The cooled solution was diluted with 130 ml diethyl ether, cooled to $\sim 10°$ and treated with 1.55 M n-butyl lithium (15.5 ml, 1.2 equiv.). The reaction mixture was heated at reflux for 1.5 hours, cooled to 0° and treated dropwise with a solution of trimethylsilyl chloride (3.1 ml, 1.2 equiv.) in 5 ml diethyl ether. The reaction mixture was stirred overnight at room temperature and then quenched with water.

The aqueous phase was extracted with ethyl acetate and the combined organics washed with brine, dried and concentrated in vacuo. Chromatography on silica gel and recrystallization from ethanol gave the title compound (3.9 g), m.p. 72°–74°. Infrared and NMR spectra were consistent with the assigned structure. MS 368($M^+$), 353 ($M-CH_3$).

EXAMPLE 2

2,3-Bis(4-methoxyphenyl)-5-(dimethylsilyl)thiophene (a) 2,3-Bis(4-methoxyphenyl)thiophene (5.92 g, 20 mmole) was dissolved in 100 ml toluene and the volume reduced by approximately ¾ by distillation. The cooled solution was diluted with 130 ml diethyl ether, cooled to 10° and treated with 1.6 M n-butyl lithium (13.5 ml, 1.1 equiv.). The reaction mixture was heated at reflux for 1.5 hours, cooled to 0° and treated dropwise with a solution of dimethylchlorosilane (3.3 ml, 1.5 equiv.) in 5 ml diethyl ether. The reaction mixture was stirred for 1.25 hours at 0° and then quenched with water.

The aqueous phase was extracted with ethyl acetate and the combined organics washed with brine, dried and concentrated in vacuo. Chromatography on silica gel gave the title compound (2.4 g) as an oil. Infrared and NMR spectra were consistent with the assigned structure.

(b) A solution of 2,3-bis(4-methoxyphenyl)thiophene (5.92 g, 20 mmole) in 100 ml diethyl ether/20 ml toluene was treated with 1.6 M n-butyl lithium (14 ml, 1.12 equiv.) and heated at reflux for 1.5 hours. The reaction mixture was cooled to $-76°$ and cannulated into a solution of dimethyldichlorosilane (4.6 ml, 1.9 equiv.) in 40 ml diethyl ether at $-76°$. After 2.5 hours, the reaction mixture was treated with a diisobutylaluminum hydride tetramethylethylenediamine complex prepared by addition of tetramethylethylenediamine (9.9 ml, 66 mmole) to 1 M diisobutylaluminum hydride in hexane (66 ml, 66 mmole). The reaction mixture was stirred 2 hours at 0°, recooled to $-30°$ and quenched with saturated aqueous potassium-sodium tartrate.

The mixture was diluted with water and ethyl acetate and filtered through a celite pad. The filtrate was partitioned between ethyl acetate and water. The combined organics were then washed with 1 N hydrochloric acid, and brine, dried and concentrated in vacuo. Chromatography on silica gel gave the title compound (2.7 g) as an oil, spectroscopically and chromatographically identical to material prepared in (a).

EXAMPLE 21

2,3-Bis(4-methoxyphenyl)-5-(methoxydimethylsilyl)thiophene

A solution of 2,3-bis(4-methoxyphenyl)thiophene (5.92 g, 20 mmole) in 100 ml toluene was concentrated by 60 ml by distillation. The cooled solution was diluted with 130 ml diethyl ether, treated with 1.6 M n-butyl lithium (14 ml, 1.1 equiv.) and heated at reflux for 1.5 hours. The reaction mixture was then cooled to $-76°$ and cannulated into a solution of dimethyldichlorosilane (4.8 ml, 40 mmole) in 40 ml diethyl ether at $-76°$. After 2.5 hours, the reaction mixture was treated dropwise with a solution of triethylamine (11 ml, 80 mmole) and methanol (3.2 ml, 80 mmole) in 10 ml diethyl ether. After 1 hour, the reaction mixture was diluted with ethyl acetate, washed with cold water and brine, dried and concentrated in vacuo.

Chromatography on silica gel gave the title compound (2.1 g) as an oil. Infrared and NMR spectra were consistent with the assigned structure. MS 384 ($M^+$).

The compounds of Examples 1 and 2, other 2,3-diaryl-5-silyl thiophenes that were prepared following the procedures described above, and other compounds that can be prepared by those procedures are shown in Table I.

TABLE I

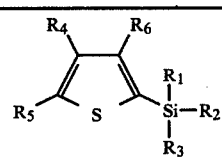

| Ex. No. | $R_1$ | $R_2$ | $R_3$ | $R_4$ | $R_5$ | $R_6$ | m.p. (°C.) |
|---|---|---|---|---|---|---|---|
| 1 | $CH_3$ | $CH_3$ | $CH_3$ | 4-$CH_3O\phi$ | 4-$CH_3O\phi$ | H | 72–74° |
| 2 | $CH_3$ | $CH_3$ | H | 4-$CH_3O\phi$ | 4-$CH_3O\phi$ | H | oil |
| 3 | $CH_3$ | $CH_3$ | $CH_3$ | 4-F$\phi$ | 4-F$\phi$ | H | 112–114° |
| 4 | $CH_3$ | $CH_3$ | $CH_3$ | $\phi$ | $\phi$ | H | 82–84° |
| 5 | $CH_3$ | $CH_3$ | $CH_3$ | 4-$CH_3\phi$ | 4-$CH_3\phi$ | H | 82.5–83.5° |
| 6 | $CH_3$ | $CH_3$ | $CH_3$ | 4-F$\phi$ | 4-$CH_3S\phi$ | H | 81–84° |

TABLE I-continued

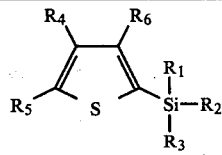

| Ex. No. | $R_1$ | $R_2$ | $R_3$ | $R_4$ | $R_5$ | $R_6$ | m.p. (°C.) |
|---|---|---|---|---|---|---|---|
| 7 | $CH_3$ | $CH_3$ | $CH=CH_2$ | 4-$CH_3O\phi$ | 4-$CH_3O\phi$ | H | 74–76.5° |
| 8 | $CH_3$ | $CH_3$ | $CH_2-CH=CH_2$ | 4-$CH_3O\phi$ | 4-$CH_3O\phi$ | H | oil |
| 9 | $CH_3$ | $CH_3$ | $CH_2CH_2CF_3$ | 4-$CH_3O\phi$ | 4-$CH_3O\phi$ | H | oil |
| 10 | $C_2H_5$ | $C_2H_5$ | $C_2H_5$ | 4-$CH_3O\phi$ | 4-$CH_3O\phi$ | H | oil |
| 11 | $CH_3$ | $CH_3$ | t-$C_4H_9$ | 4-$CH_3O\phi$ | 4-$CH_3O\phi$ | H | oil |
| 12 | $CH_3$ | $CH_3$ | $\phi$ | 4-$CH_3O\phi$ | 4-$CH_3O\phi$ | H | oil |
| 13 | $CH_3$ | $CH_3$ | $CH_2\phi$ | 4-$CH_3O\phi$ | 4-$CH_3O\phi$ | H | oil |
| 14 | $CH_3$ | H | H | 4-$CH_3O\phi$ | 4-$CH_3O\phi$ | H | oil |
| 15 | $CH_3$ | $CH_3$ | n-$C_7H_{15}$ | 4-$CH_3O\phi$ | 4-$CH_3O\phi$ | H | |
| 16 | $CH_3$ | $CH_3$ | $CH_3$ | 4-$CH_3O\phi$ | 4-$(CH_3)_2N\phi$ | H | |
| 17 | $CH_3$ | $CH_3$ | $CH_3$ | 4-$CH_3O\phi$ | 3-Pyridyl | H | |
| 18 | $CH_3$ | $CH_3$ | $CH_3$ | 4-$Cl\phi$ | 4-$CH_3O\phi$ | H | |
| 19 | $CH_3$ | $CH_3$ | $CH_3$ | 4-$F\phi$ | 4-$F\phi$ | $CH_3$ | |
| 20 | $CH_3$ | $CH_3$ | $CH=CH_2$ | 4-$C_2H_5O\phi$ | 4-$CH_3O\phi$ | H | |
| 21 | $CH_3$ | $CH_3$ | $CH_3O$ | 4-$CH_3O\phi$ | 4-$CH_3O\phi$ | H | oil |
| 22 | $CH_3$ | $CH_3O$ | $CH_3O$ | 4-$CH_3O\phi$ | 4-$CH_3O\phi$ | H | |
| 23 | $CH_3$ | $CH_3$ | $C_2H_5O$ | 4-$CH_3O\phi$ | 4-$CH_3O\phi$ | H | |
| 24 | $CH_3$ | $CH_3$ | $CH_3$ | 4-$CH_3O\phi$ | 4-$CH_3\underset{\underset{O}{\|}}{\overset{\overset{O}{\|}}{S}}\phi$ | H | |
| 25 | $CH_3$ | $CH_3$ | $C_5H_{10}CH=CH_2$ | 4-$CH_3O\phi$ | 4-$CH_3O\phi$ | H | |
| 26 | $CH_3$ | $CH_3$ | $CH_3$ | 4-$C_2H_5\phi$ | 4-$C_2H_5\phi$ | H | |
| 27 | $CH_3$ | $CH_3$ | $C_2H_5$ | 4-$CH_3O\phi$ | 4-$CH_3O\phi$ | H | 65–67° |
| 28 | $CH_3$ | $CH_3$ | $CH_3$ | 4-$CH_3O\phi$ | 4-$C_2H_5S\phi$ | H | |
| 29 | $CH_3$ | $CH_3$ | $CH_3$ | 4-$CH_3O\phi$ | 4-$(C_2H_5)_2N\phi$ | H | |

Dosage Forms

The antiinflammatory and/or analgesic agents of this invention can be administered to treat inflammation and/or relieve pain by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.5 to 50, and preferably 1 to 25 milligrams per kilogram per day given in divided doses 1 to 6 times a day or in sustained release form is effective to obtain desired results.

Dosage forms (compositions) suitable for internal administration contain from about 1 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl or propyl-paraben, and chlorobutanol.

Suitable pharmaceutical carriers are described in *Remington's Pharmaceutical Sciences*, E. W. Martin, a standard reference text in this field.

Useful pharmaceutical dosage forms for administration of the compounds of this invention can be illustrated as follows:

Capsules

A large number of unit capsules are prepared by filling standard two-piece hard gelatin capsules each with 75 milligrams of powdered active ingredient, 150 milligrams of lactose, 24 milligrams of talc, and 6 milligrams magnesium stearate.

Soft Gelatin Capsules

A mixture of active ingredient in soybean oil is prepared and injected by means of a positive displacement pump into gelatin to form soft gelatin capsules containing 75 milligrams of the active ingredient. The capsules were washed in petroleum ether and dried.

Tablets

A large number of tablets are prepared by conventional procedures so that the dosage unit is 75 milligrams of active ingredient, 6 milligrams of magnesium stearate, 70 milligrams of microcrystalline cellulose, 11 milligrams of cornstarch and 200 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is sterilized by commonly used techniques.

Suspension

An aqueous suspension is prepared for oral administration so that each 5 milliliters contain 25 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

Injectable

A parenteral composition suitable for administration by injection is prepared by dissolving 1% by weight of active ingredient in sodium chloride injection U.S.P. XX and adjusting the pH of the solution to between 6 and 7. The solution is sterilized by commonly used techniques.

Use

To detect and compare the antiinflammatory activities of compounds in this series and standard drugs, a test was used based on a standard model of arthritis for which there is good correlation with human efficacy. The model is adjuvant-induced arthritis in rats. *Federation Proceedings*, Vol. 32, No. 2, 1973 "Models Used for the Study and Therapy of Rheumatoid Arthritis'-'—Symposium of the American Society for Pharmacology and Experimental Therapeutics—states "The rat polyarthritis produced by intradermal injection of a suspension of *Mycobacterium tuberculosis* in mineral oil (adjuvant) has been used extensively for the screening of drugs of potential use in rheumatoid arthritis."

Established Adjuvant-Induced Arthritis in Rats

Charles River Lewis male rats (130–150 grams) are injected subcutaneously in the plantar area of the right hind paw with 0.1 ml of adjuvant (Difco heat-killed, lyophilized *Mycobacterium butyricum* suspended in mineral oil 5 mg/ml). 20 Non-arthritic controls are injected with mineral oil. The animals are held for 2 weeks to allow development of arthritis. Paw volumes (uninjected, left hind paw) are measured and the adjuvant-injected rats are culled and distributed to treatment groups of 10 of equal disease severity. Non-arthritic controls are distributed to 2 groups of 10. The rats are given oral doses of compound or PVA-Acacia (Polyvinyl Alcohol 1%, Gum acacia, U.S.P. 5%, Methylparaben 0.5%) (10 ml/kg) by gavage on that day and on the 6 following days. One day after the last dose the paw volumes (uninjected, left hind paw) are measured using a Ugo Basile Volume Differential Meter Model 7101.

$$\frac{\text{Arthritic Control} \quad \text{Treatment Group}}{\text{Mean Paw Volume (ml)} - \text{Mean Paw Volume (ml)}} \times 100 =$$
$$\frac{\text{Arthritic Control} \quad \text{Non-Arthritic Control}}{\text{Mean Paw Volume (ml)} - \text{Mean Paw Volume (ml)}}$$

% Decrease from Control Mean Paw Volume.

Dose-response regression lines of the percent decrease are plotted on semi-log paper by visual fit and the ED50% decrease from control paw volume is determined by inspection. Data for some of the compounds in this invention are summarized in Tables II and III.

Compounds from this series were also compared to indomethacin, phenylbutazone, ibuprofen, and aspirin.

Phenylquinone Writhing Test

A standard procedure for detecting and comparing the analgesic activity of compounds in this series for which there is a good correlation with human efficacy is the standard phenylquinone writhing test modified from Siegmund, et al., *Proc. Soc. Exp. Biol. Med.*, 95, 729 (1957). A test compound suspended in 1% methylcellulose was given orally to fasted (17–21 hours) female white mice, 5–20 animals per double blind test. Aqueous (0.01% phenyl-p-benzoquinone) phenylquinone, 0.20 ml per mouse, was injected intraperitoneally 6 minutes before observations were begun. At an appropriate time after the oral administration of the test compound, the mice were observed for 10 minutes for a characteristic stretching or writhing syndrome which is indicative of pain induced by phenylquinone. The effective analgesic dose for 50% of the mice ($ED_{50}$) was calculated by the moving average method of Thompson, W. R., *Bact. Rev.*, 11, 115–145 (1947); the time of peak activity was determined for many of the compounds. Data for some of the compounds is summarized in Tables II and III together with data for some standard analgetic antiinflammatory drugs.

TABLE II

| Compound Ex. No. | Daily Oral Dose (mg/kg) | Adjuvant Arthritis Percent Decrease From Control Paw Volume | Phenylquinone Writhing $ED_{50}$ (mg/kg) |
|---|---|---|---|
| 3 | 27 | 37[1] | 4.5 |
| 5 | 45 | 44[1] | 135 |
| 6 | 81 | 42[1] | — |

TABLE II-continued

| Compound Ex. No. | Daily Oral Dose (mg/kg) | Adjuvant Arthritis Percent Decrease From Control Paw Volume | Phenylquinone Writhing $ED_{50}$ (mg/kg) |
| --- | --- | --- | --- |
| 13 | 45 | 24[2] | — |

[1] $p < .001$ compared to control by Student's "t" test.
[2] $p < .05$ compared to control by Student's "t" test.

TABLE III

| Compound Ex. No. | Adjuvant Arthritis $ED_{50}$% Decrease From Control Paw Volume (mg/kg) | Phenylquinone Writhing $ED_{50}$ (mg/kg) |
| --- | --- | --- |
| 1 | 8 | 0.19 |
| 2 | 14.5 | 2.1 |
| 4 | 45 | 15 |
| 7 | 6.8 | 0.23 |
| 8 | 9.4 | 0.76 |
| 9 | 30 | — |
| 10 | 25 | 5.2 |
| 11 | 40 | >108 |
| 12 | 55 | <108 |
| 21 | 9.8 | 3.8 |
| Indomethacin | 0.3 | 0.35 |
| Phenylbutazone | 10 | 80 |
| Ibuprofen | 100 | 10 |
| Aspirin | 305 | 135 |

"Consisting essentially of" in the present disclosure is intended to have its customary meaning: namely, that all specified material and conditions are very important in practicing the invention but that unspecified materials and conditions are not excluded so long as they do not prevent the benefits of the invention from being realized.

What is claimed is:

1. A compound having the formula:

$$\underset{R_5}{\overset{R_4}{\diagup}}\!\!\!\underset{S}{\diagdown}\!\!\!\underset{}{\overset{R_6}{\diagup}}\!\!\!\underset{}{\overset{R_1}{\underset{R_3}{\overset{|}{Si}-R_2}}}$$

wherein $R_1$, $R_2$ and $R_3$ are independently H, alkoxy of 1–2 carbon atoms, alkyl of 1–7 carbon atoms optionally substituted with halogen, alkenyl of 2–7 carbon atoms, phenyl or benzyl, with the proviso that the sum of the number of carbon atoms in $R_1$, $R_2$ and $R_3$ must be at least 1 and not greater than 9 with the additional proviso that no more than 2 of $R_1$, $R_2$ and $R_3$ are alkoxy;

$R_4$ and $R_5$ are independently pyridyl or $$X-\!\!\left\langle\!\!\bigcirc\!\!\right\rangle\!\!-$$

where X is H, F, Cl, $R_7$, $OR_7$, $S(O)_nR_7$ or $$-N\!\!\underset{R_8}{\overset{R_7}{\diagdown}}$$

where $n = 0$, 1 or 2; $R_7$ = alkyl of 1–2 carbon atoms and $R_8$ = alkyl of 1–2 carbon atoms;

with the proviso that $R_4$ and $R_5$ cannot both be $$Cl-\!\!\left\langle\!\!\bigcirc\!\!\right\rangle\!\!-;\text{ and}$$

with the further proviso that when $R_1$, $R_2$ or $R_3$ is alkoxy, both $R_4$ and $R_5$ are $$X-\!\!\left\langle\!\!\bigcirc\!\!\right\rangle\!\!-,$$

then X cannot be H or $R_7$; and $R_6$ is H, or alkyl of 1–2 carbon atoms; or a pharmaceutically suitable salt thereof.

2. A compound of claim 1 wherein $R_6$ is H.

3. A compound of claim 2 wherein $R_4$ and $R_5$ are independently $$X-\!\!\left\langle\!\!\bigcirc\!\!\right\rangle\!\!-$$

where X = H, $OR_7$ or $(CH_3)_2N$— with the proviso that one X must be other than H.

4. A compound of claim 2 wherein $R_1$, $R_2$ and $R_3$ are independently H, alkyl of 1–3 carbon atoms, or alkenyl of 2–3 carbon atoms, with the proviso that the sum of the number of carbon atoms in $R_1$, $R_2$ and $R_3$ must be at least 2 and not greater than 5.

5. A compound of claim 2 wherein $R_4$ and $R_5$ are independently $$X-\!\!\left\langle\!\!\bigcirc\!\!\right\rangle\!\!-$$

where X = $OR_7$; and $R_1$, $R_2$ and $R_3$ are independently H, alkyl of 1–3 carbon atoms, or alkenyl of 2–3 carbon atoms, with the proviso that the sum of the number of carbon atoms in $R_1$, $R_2$ and $R_3$ must be at least 2 and not greater than 5.

6. A compound of claim 2 wherein $R_4$ and $R_5$ are $$CH_3O-\!\!\left\langle\!\!\bigcirc\!\!\right\rangle\!\!-;\text{ and}$$

$R_1$, $R_2$ and $R_3$ are independently alkyl of 1–2 carbon atoms or alkenyl of 2–3 carbon atoms, with the proviso that the sum of the number of carbon atoms in $R_1$, $R_2$ and $R_3$ is no greater than 5.

7. The compound of claim 2 which is 2,3-bis-(4-methoxyphenyl)-5-(trimethylsilyl)thiophene.

8. The compound of claim 2 which is 2,3-bis-(4-methoxyphenyl)-5-(ethenyldimethylsilyl)thiophene.

9. The compound of claim 2 which is 2,3-bis-(4-methoxyphenyl)-5-[(2-propenyl)dimethylsilyl]thiophene.

10. A pharmaceutical composition consisting essentially of a suitable pharmaceutical carrier and an effective antiinflammatory or analgesic amount of at least one compound of claim 1 or claim 2 or claim 3 or claim 4 or claim 5 or claim 6 or claim 7 or claim 8 or claim 9.

11. A method of treating inflammation, pain or both in a mammal which comprises administering to a mammal afflicted with inflammation, pain or both an effective antiinflammatory or analgesic amount of at least one compound of the formula:

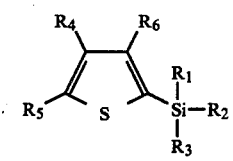

wherein $R_1$, $R_2$ and $R_3$ are independently H, alkoxy of 1–2 carbon atoms, alkyl of 1–7 carbon atoms optionally substituted with halogen, alkenyl of 2–7 carbon atoms, phenyl or benzyl, with the proviso that the sum of the number of carbon atoms in $R_1$, $R_2$ and $R_3$ must be at least 1 and not greater than 9 with the additional proviso that no more than 2 of $R_1$, $R_2$ and $R_3$ are alkoxy;

$R_4$ and $R_5$ are independently pyridyl or

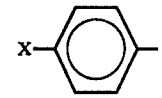

where X is H, F, Cl, $R_7$, $OR_7$, $S(O)_nR_7$ or

where $n=0$, 1 or 2; $R_7$=alkyl of 1–2 carbon atoms and $R_8$-alkyl of 1–2 carbon atoms;

with the proviso that $R_4$ and $R_5$ cannot both be

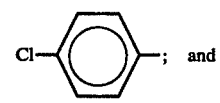 ; and $R_6$ is H, or alkyl of 1–2 carbon atoms; or a pharmaceutically suitable salt thereof.

12. A method of treating inflammation, pain or both in a mammal which comprises administering to a mammal afficted with inflammation, pain or both an effective antiinflammatory or analgesic amount of at least one compound of claim 1 or claim 2 or claim 3 or claim 4 or claim 5 or claim 6 or claim 7 or claim 8 or claim 9.

* * * * *